US00PP08861P

United States Patent [19]

Starkl

[11] Patent Number: Plant 8,861

[45] Date of Patent: Aug. 16, 1994

[54] HYBRID TEA ROSE PLANT NAMED 'STARQUELI'

[75] Inventor: Ludwig Starkl, Vienna, Austria

[73] Assignee: Bear Creek Gardens, Inc., Medford, Mich.

[21] Appl. No.: 88,841

[22] Filed: Jul. 6, 1993

[51] Int. Cl.[5] ..... A01H 5/00

[52] U.S. Cl. ..... Plt./16

[58] Field of Search ..... Plt. 15, 16, 17, 25, Plt. 22

*Primary Examiner*—Howard J. Locker

*Attorney, Agent, or Firm*—Klarquist Sparkman Campbell Leigh & Whinston

[57] ABSTRACT

A sport of the rose variety AROyqueli having a distinct and uniform color difference from its parent.

1 Drawing Sheet

The present invention relates to a new and distinct variety of rose plant of the hybrid tea class which was discovered by me as a mutation of the variety AROyqueli, U.S. Plant Pat. No. 5,177.

This variety is unique and distinct from the original variety AROyqueli in its flower color. Instead of having petals of color Yellow-Orange 15B and Yellow-Orange 14C on the petal outside, STARqueli has a color of Orange Group 25B. The petal inside is Orange 25B that blushes to Orange 25D in sunlight. Otherwise, this new variety is identical in all other respects to AROyqueli.

Asexual reproduction of this new variety by budding, as performed at Wasco, Calif., shows that the foregoing characteristics and distinctions come true to form and are established and transmitted through succeeding propagations.

The accompanying illustration shows typical flowers of this new variety and of its parent in different stages of development, depicted in color as nearly true as it is reasonably possible to make the same in a color illustration of this character.

Since the plant is otherwise the same as that of its parent AROyqueli, the description will be limited to the flower characteristics of this new variety. This description of my new rose cultivar will be with color descriptions using terminology in accordance with The Royal Horticultural Society (London) Colour Chart, except where ordinary dictionary significance of color is indicated.

FLOWER

Observations made from specimens grown in Somis, Calif., from March-June of 1992.

Blooming habit.—Recurrent.

Bud:

*Size.*—1½" when the petals start to unfurl.

*Form.*—Long, pointed ovoid.

*Color.*—When sepals first divide, bud color is Orange Group 25B. When half blown, the upper sides of the petals are Orange Group 25B; and the lower sides of the petals are Orange Group 25B.

*Sepals.*—Color: Green Group 138B. Surface texture: Covered with fine hairs. There are three normal to heavily appendaged sepals. There are two unappendaged sepals with hairy edges.

*Receptacle.*—Color: Green Group 137C. Shape: Funnel. Size: Small, ¼"×¼". Surface: Smooth.

*Peduncle.*—Length: Short. Surface: Smooth, glandular. Color: Medium green. Strength: Stiff, erect.

Bloom:

*Size.*—Large. Average open size is 4½".

*Borne.*—Singly and several together, in clusters. If in clusters: Flat.

*Stems.*—Long, 16" to 20".

*Form.*—When first open: High centered. Permanence: Retains its form to the end, outer petals curl back.

*Petalage.*—Number of petals under normal conditions: 35.

*Color.*—The upper side of the petals is Orange Group 25B. The reverse side of the petals is Orange Group 25B. The bases of the petals have a yellow half moon (¼×¼") at the point of attachment. The major color on the upper side is Orange Group 25B.

*Variegations.*—None.

*Discoloration.*—The general tonality at the end of the first day: No change. At the end of the third day: Some blushing to Orange Group 25D as petals reflex.

*Fragrance.*—Moderate.

Petals:

*Texture.*—Medium.

*Shape.*—Round.

*Form.*—Tips slightly recurved.

*Arrangement.*—Imbricated, with few petaloids in the center.

*Persistence.*—Drops off cleanly.

*Lastingness.*—On the plant: fair, 3-5 days. As a cut flower: fair, 5-6 days.

Reproductive parts:

*Anthers.*—Size: Medium. Color: Yellow. Arrangement: Regular around styles, mixed with occasional petaloids.

*Filaments.*—Color: Yellow.

*Pollen.*—Color: Golden yellow.

*Styles.*—Color: Reddish.

*Stigmas.*—Color: Greenish white.

I claim:

1. A new and distinct variety of rose plant of the hybrid tea class, substantially as herein shown and described, a sport of the variety AROyqueli characterized particularly as to novelty by its distinct and uniform flower color difference from its parent.

* * * * *

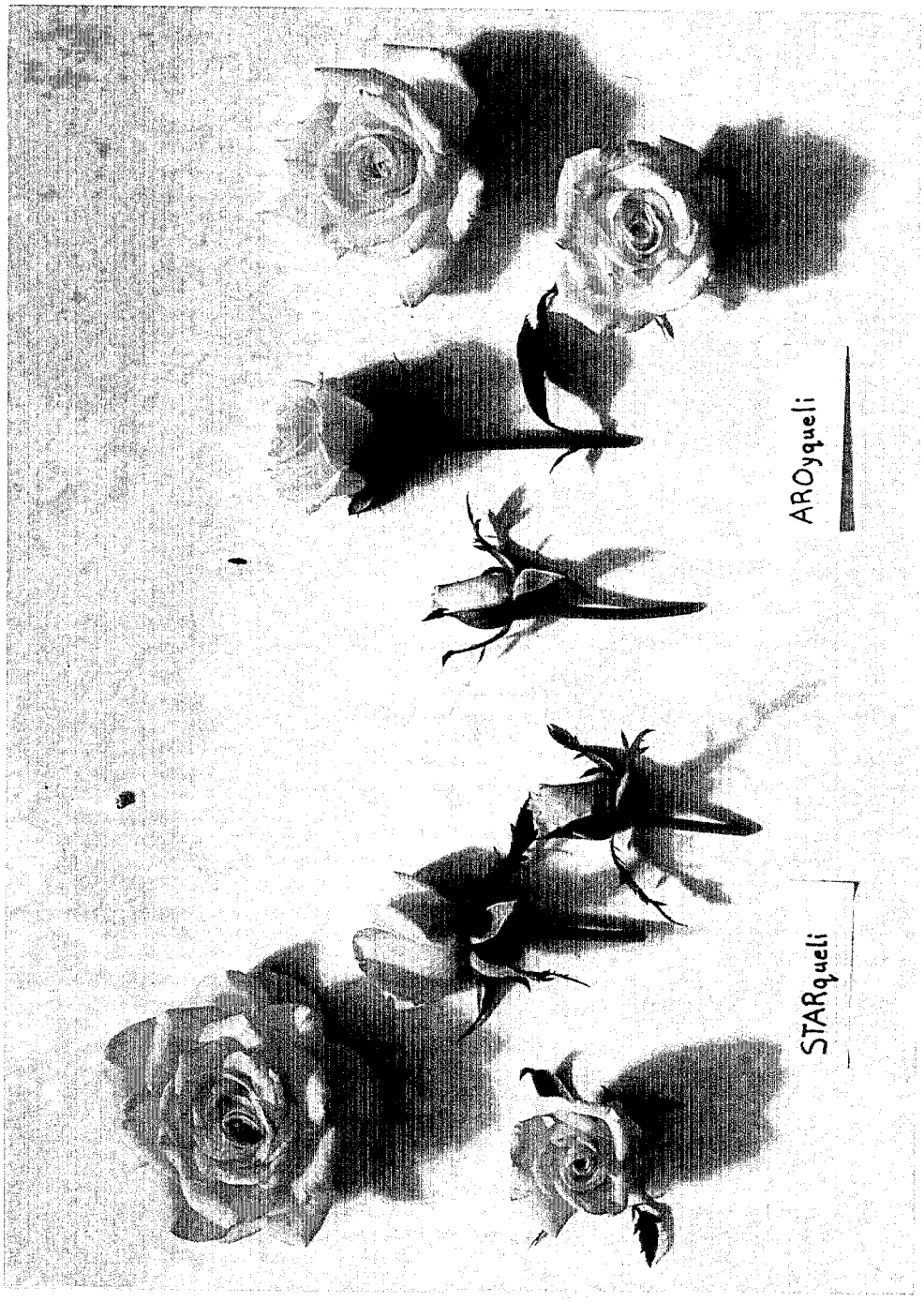
STARqueli
ARQyqueli